US011490900B2

(12) United States Patent
Goto et al.

(10) Patent No.: US 11,490,900 B2
(45) Date of Patent: Nov. 8, 2022

(54) OSTEOTOMY ASSISTANCE KIT

(71) Applicants: Makoto Goto, Nishinomiya (JP);
Tsuyoshi Murase, Toyonaka (JP)

(72) Inventors: Makoto Goto, Nishinomiya (JP);
Tsuyoshi Murase, Toyonaka (JP)

( * ) Notice: Subject to any disclaimer, the term of this patent is extended or adjusted under 35 U.S.C. 154(b) by 522 days.

(21) Appl. No.: 16/490,327

(22) PCT Filed: Mar. 3, 2017

(86) PCT No.: PCT/JP2017/008630
§ 371 (c)(1),
(2) Date: Aug. 30, 2019

(87) PCT Pub. No.: WO2018/158962
PCT Pub. Date: Sep. 7, 2018

(65) Prior Publication Data
US 2020/0000479 A1     Jan. 2, 2020

(51) Int. Cl.
*A61B 17/15* (2006.01)
*A61B 17/56* (2006.01)
(Continued)

(52) U.S. Cl.
CPC ............ *A61B 17/151* (2013.01); *A61B 34/10* (2016.02); *A61B 2017/568* (2013.01);
(Continued)

(58) Field of Classification Search
CPC ............ A61B 17/151; A61B 2017/568; A61B 2090/061; A61B 17/15
See application file for complete search history.

(56) References Cited

U.S. PATENT DOCUMENTS 4,938,762 A * 7/1990 Wehrli ................. A61B 17/154
606/88
6,711,432 B1 3/2004 Krause et al.
(Continued)

FOREIGN PATENT DOCUMENTS

EP     2749257 A1    7/2014
EP     3069671 A1    9/2016
(Continued)

OTHER PUBLICATIONS

Extended European Search Report dated Mar. 5, 2021 mailed in the corresponding European Patent Application No. 17898699.8.
(Continued)

*Primary Examiner* — David W Bates
(74) *Attorney, Agent, or Firm* — IP Business Solutions, LLC

(57) ABSTRACT

An osteotomy assistance kit includes a bone treatment assistance device and an attaching position confirmation device. The attaching position confirmation device includes a feature point indication rod to be applied via a tip portion to a feature point of the bone, a rod support unit that removably supports the feature point indication rod such that the tip portion is indicating the feature point of the bone, and a second support member that movably supports the rod support unit and indicates one of scales on the rod support unit. The bone treatment assistance device includes cutting slits, and first guide holes that guides first rods set to a predetermined positional relation. The second support member of the attaching position confirmation device is attached to the protrusion of the bone treatment assistance device.

2 Claims, 21 Drawing Sheets

(51) Int. Cl.
  *A61B 90/00* (2016.01)
  *A61B 34/10* (2016.01)
  *B33Y 50/02* (2015.01)
(52) U.S. Cl.
  CPC ... *A61B 2034/104* (2016.02); *A61B 2034/105* (2016.02); *A61B 2090/061* (2016.02); *B33Y 50/02* (2014.12); *G05B 2219/35134* (2013.01); *G05B 2219/49007* (2013.01)

(56) References Cited

U.S. PATENT DOCUMENTS

| | | |
|---|---|---|
| 2005/0273112 A1 | 12/2005 | McNamara |
| 2006/0195111 A1 | 8/2006 | Couture |
| 2006/0217733 A1 | 9/2006 | Plassky et al. |
| 2007/0173815 A1* | 7/2007 | Murase .................. A61B 17/15 606/53 |
| 2007/0232959 A1 | 10/2007 | Couture et al. |
| 2007/0244488 A1 | 10/2007 | Metzger et al. |
| 2013/0085500 A1* | 4/2013 | Meridew ................ A61B 34/10 606/89 |
| 2014/0188236 A1 | 7/2014 | McGinley et al. |
| 2016/0287335 A1* | 10/2016 | Goto ...................... A61B 34/10 |
| 2018/0085133 A1* | 3/2018 | Lavallee ............. A61B 17/1764 |
| 2018/0368860 A1* | 12/2018 | Wodajo .............. A61B 17/1703 |

FOREIGN PATENT DOCUMENTS

| | | |
|---|---|---|
| JP | 2014-030536 A | 2/2014 |
| JP | 5749788 B2 | 7/2015 |
| JP | 2016-140487 A | 8/2016 |
| WO | 2014152535 A1 | 9/2014 |
| WO | 2015072187 A1 | 5/2015 |

OTHER PUBLICATIONS

Partial Supplementary European Search Report dated Oct. 19, 2020 mailed in the corresponding European Patent Application No. 17898699.8.

International Search Report dated Apr. 4, 2017 issued in corresponding PCT/JP2017/008630 application.

* cited by examiner

OSTEOTOMY ASSISTANCE KIT

TECHNICAL FIELD

The present invention relates to an attaching position confirmation device, an osteotomy assistance kit, and a position detection program, to be used to cut or perforate a bone deformed by bone fracture or the like, to thereby correct the bone.

BACKGROUND ART

Treatment of deformation of a human body due to bone fracture includes cutting a bone as required for correction, and moving or rotating the cut bone pieces to a target correction position. To perform these processes with high accuracy, Patent Literature (PTL) 1 cited below proposes a bone treatment assistance device to be used for osteotomy. The bone treatment assistance device is configured to cut a bone deformed into an abnormal condition at a target position accurately, thereby allowing the bone to be divided into bone pieces, and securely move the bone pieces obtained by the cutting to a position to constitute a bone of a normal condition. The bone treatment assistance device includes a fitting surface that fits the surface of the bone to be treated, and the bone treatment assistance device is attached to the position corresponding to the cutting cross-section, by attaching the bone treatment assistance device such that the fitting surface fits the shape of the bone surface. Then, when a rod, inserted through a guide hole of the bone treatment assistance device, is thrust into a feature point of the bone to be treated, it can be confirmed that the bone treatment assistance device is attached to the target position of the bone.

CITATION LIST

Patent Literature

PTL 1: International Publication No. WO2015-072187

SUMMARY OF INVENTION

Technical Problem

With the bone treatment assistance device according to PTL 1, however, it is necessary to insert the rod through the guide hole, and actually thrust the rod into the feature point, to check whether the bone treatment assistance device is attached to the target position on the bone to be treated, at the time of the surgery. Accordingly, the bone is subjected to a burden, and besides a troublesome operation to thrust the rod into the feature point is required, to check whether the bone treatment assistance device is attached to the target position. Further, although the rod is thrust into the feature point, it is difficult for the surgeon to objectively recognize whether the tip portion of the rod is accurately thrust into the feature point, or to what extent the rod is deviated therefrom. Thus, it is difficult for the surgeon to objectively recognize whether the bone treatment assistance device is accurately attached to, or to what extent the bone treatment assistance device is deviated from, the target position on the bone to be treated.

The present invention has been accomplished in view of the foregoing drawbacks, and provides a technique to recognize how accurately the bone treatment assistance device is attached to the target position on the bone to be treated, with a reduced impact on the bone, and with reduced workload.

Solution to Problem

In an aspect, the present invention provides an attaching position confirmation device, to be attached to a bone treatment assistance device employed to assist a cutting or perforating operation of a bone, to confirm the attaching position of the bone treatment assistance device on the bone. The attaching position confirmation device includes a feature point indication rod to be applied via a tip portion to a predetermined specific feature point of the bone, a rod support unit including a rod support member that supports the feature point indication rod in a posture that allows the tip portion to indicate the feature point of the bone, and an elongate member extending in an elongate shape from the rod support member, and including a plurality of scales provided at different positions along an extending direction, and a second support member that supports, when attached to the bone treatment assistance device attached to the bone, the rod support unit so as to move in the extending direction, and indicates one of the plurality of scales.

In another aspect, the present invention provides an osteotomy assistance kit including the attaching position confirmation device, and a bone treatment assistance device. The bone treatment assistance device includes a cutting slit formed at a position corresponding to a cutting cross-section, where a bone is cut and divided when the bone treatment assistance device is attached to a surface of the bone, to guide a cutting jig to the cutting cross-section, guide holes each guides, after bone pieces cut and divided along the cutting cross-section are corrected into a positional relation to be realized under a normal condition, a first rod to be inserted in the bone when the bone treatment assistance device is attached to the surface of the bone, in a posture that the first rod inserted in the bone piece assumes a predetermined positional relation with respect to another first rod inserted in the bone piece, and an attaching portion where the second support member of the attaching position confirmation device is to be attached.

In still another aspect, the present invention provides a position detection program configured to cause a computer to act as a bone model generator that acquires three-dimensional data of a bone to be treated, and generates a three-dimensional bone model representing the bone to be treated, according to the three-dimensional data acquired, a bone piece model generator that determines a cutting cross-section for correction of the bone model, and generates bone piece models that can be moved or rotated to a target correction position approximate to a target bone model representing a bone into which the bone to be treated is to be corrected, the bone piece models being obtained by cutting the bone model along the cutting cross-section, a first rod model position calculator that calculates a position of each of first rod models determined when the bone piece models are located at a position of the bone model, on a basis of a position of each of the first rod models attached to the bone piece model located at the target correction position, a bone treatment assistance device model position calculator that calculates a position where a bone treatment assistance device model is to be located when attached to the bone model, the bone treatment assistance device model representing a bone treatment assistance device including a cutting slit formed at a position corresponding to the cutting cross-section to guide a cutting jig to the cutting cross-section, and guide holes in which the first rod model formed at the calculated position can be inserted, and a position detector that detects a distance from a position indicating a feature point that is a predetermined specific portion on the bone model to the bone treatment assistance device model whose portion indicating a fitting surface is attached to a position that fits to a surface shape of the bone model uncorrected yet, at a time when a rod support unit model supporting a feature point indication rod model being applied via a tip portion to the feature point is attached to a second support member model that is attached to the bone treatment assistance device model attached to the bone model.

Advantageous Effects of Invention

The foregoing configuration makes it possible to recognize how accurately the bone treatment assistance device is attached to the target position on the bone to be treated, with a reduced impact on the bone, and with reduced workload.

DESCRIPTION OF EMBODIMENT

Hereafter, an attaching position confirmation device, an osteotomy assistance kit, and a position detection program according to an embodiment of the present invention will be described, with reference to the drawings.

Figure 1A:
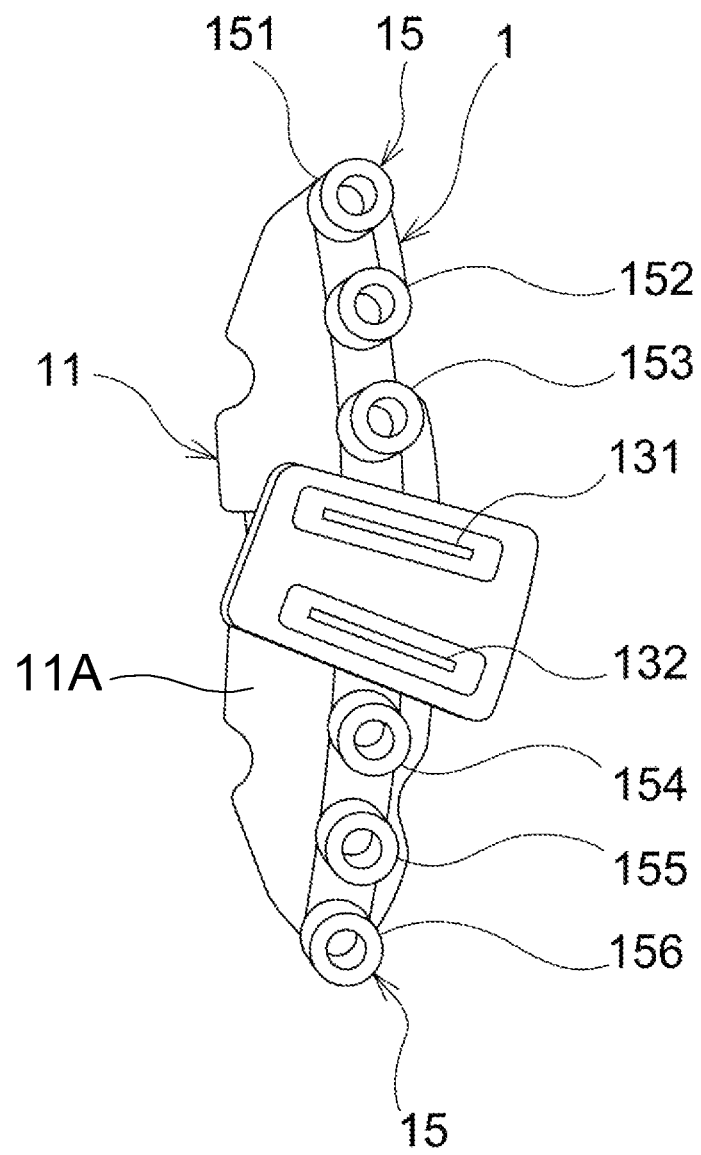
FIG. 1A is a perspective view showing a bone treatment assistance device, employed in an osteotomy assistance kit according to an embodiment of the present invention.
Figure 1B:
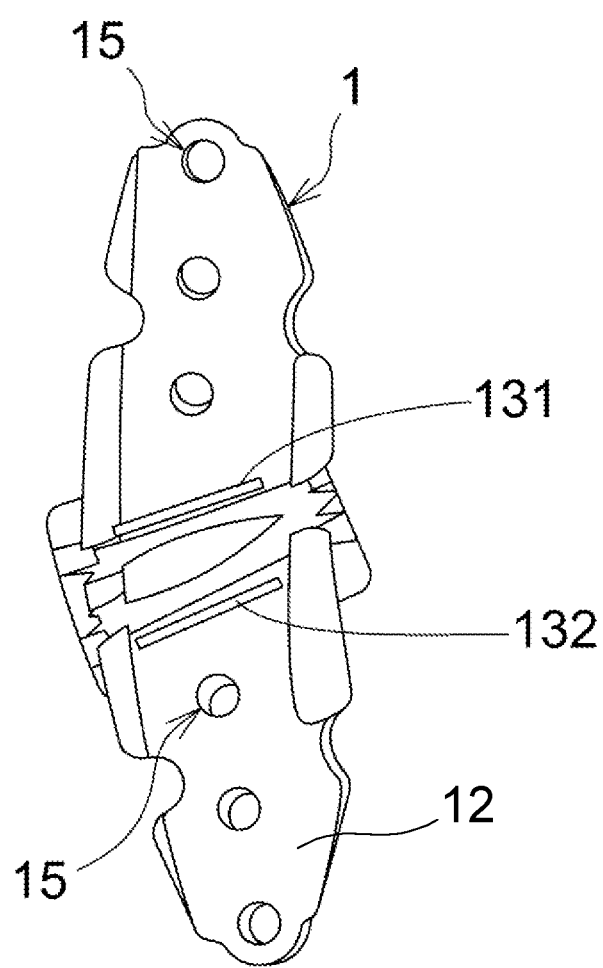
FIG. 1B is a perspective view showing a fitting surface on the back side of the bone treatment assistance device.
Figure 2:
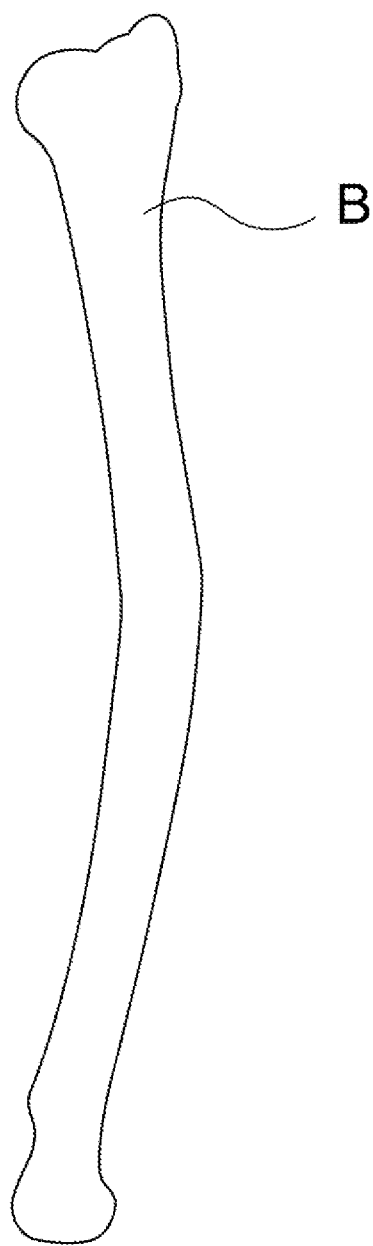
FIG. 2 is a perspective view showing a bone to be treated.
Figure 3:
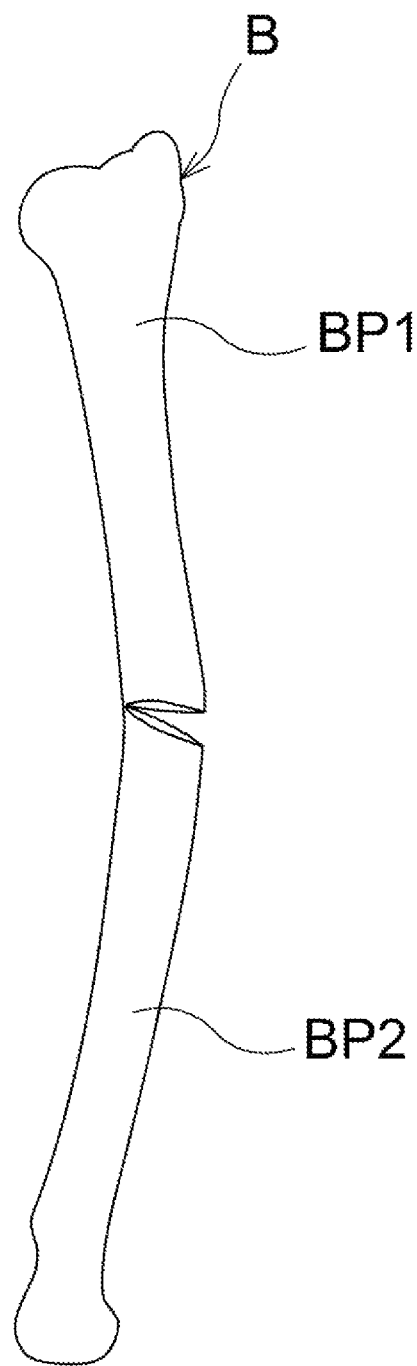
FIG. 3 is a perspective view of the bone to be treated, cut and divided into bone pieces.

FIG. 1A is a perspective view showing the bone treatment assistance device, employed in the osteotomy assistance kit according to the embodiment of the present invention. FIG. 1B is a perspective view showing a fitting surface on the back side of the bone treatment assistance device. FIG. 2 is a perspective view showing a bone to be treated. FIG. 3 is a perspective view of the bone to be treated, cut and divided into bone pieces.

Figure 4:
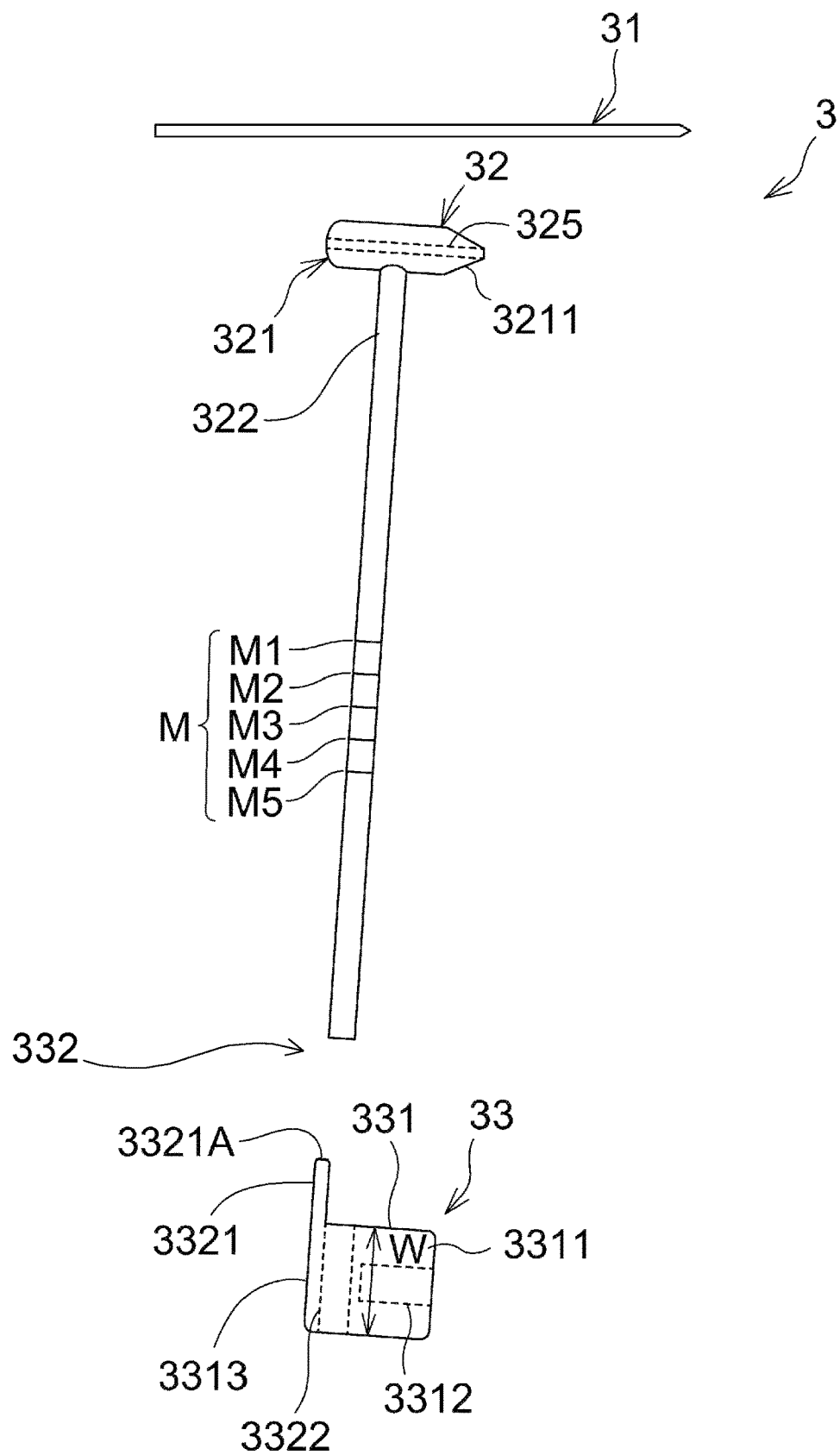
FIG. 4 is a drawing showing some parts of an attaching position confirmation device.

The osteotomy assistance kit includes a bone treatment assistance device 1 and an attaching position confirmation device 3 (see FIG. 4). In this embodiment, the bone treatment assistance device 1 is configured to cut a bone B deformed into an abnormal condition along a predetermined cutting cross-section, thereby dividing the bone B. However, the bone treatment assistance device according to the present invention is not limited to the bone treatment assistance device itself, but also includes assistance devices used for drilling of the bone, or insertion of a K wire. The bone B is divided into bone pieces BP1 and BP2, upon being cut by the bone treatment assistance device 1. Either or both of the bone pieces BP1 and BP2 are moved and/or rotated (hereinafter simply expressed as moved) by a surgeon to a target correction position representing a normal condition. The bone treatment assistance device 1 is manufactured, for example, through a rapid prototyping method such as optical modelling, or with a 3D printer, on the basis of three-dimensional model data generated and outputted through a bone treatment assistance device manufacturing program as will be subsequently described. The bone treatment assistance device 1 may be formed of a resin, for example.

The bone treatment assistance device 1 includes a main body 11, a fitting surface 12, cutting slits 131 and 132, and first guide holes 15.

The main body 11 is formed in a shape that fits the shape of the surface of a bone to be treated. The fitting surface 12 is formed on a side face of the main body 11, at a position opposing the bone B to be treated (on the back of the main body 11 shown in FIG. 1). The fitting surface 12 is formed in a shape that fits the surface shape of the bone B. The fitting surface 12 is formed on the basis of three-dimensional data of the bone B obtained, for example, through a CT process.

To acquire the three-dimensional data of the bone B, any available device may be employed provided that the three-dimensional model of the object can be obtained. Examples of applicable devices include, but are not limited to, a CCD camera, an optical camera, X-ray photography, CT, and magnet resonance imaging (MRI).

The cutting slits 131 and 132 serve as a cutting jig to guide a cut to the predetermined cutting cross-section, when the bone treatment assistance device 1 is attached to the bone B with the fitting surface fitted to the surface of the bone. The cutting slits 131 and 132 are formed on a side face of the main body 11. The cutting jig may guide, for example, an electric saw. The cutting cross-section may be a flat plane for example, which can be defined by a position on the surface of the bone B and an angle with respect to the surface of the bone B. The cutting cross-section is defined by the surgeon in advance of the operation of the bone B to be treated. The cutting slits 131 and 132 are formed in a shape that allows, when the electric saw is employed with the cutting jig, the saw blade to be inserted. The cutting slits 131 and 132 each guide the saw blade, acting as the cutting jig, to the cutting cross-section determined by the position and angle with respect to the bone B.

Each of the first guide holes 15 is formed in a shape that guides a first rod (illustrated in the drawings to be subsequently referred to) to be inserted in the bone B to a predetermined thrusting position, when the bone treatment assistance device 1 is attached to the bone B with the fitting surface fitted to the surface of the bone. The first rod is, for example, formed of a metal with a pointed tip portion, so as to be thrust into the bone. The diameter of the first rod is the same as, or slightly smaller than that of the first guide hole 15. The first guide hole 15 includes protrusions 151 to 156, extending along the path of the first rod when the first rod is thrust into the bone B.

Figure 20:
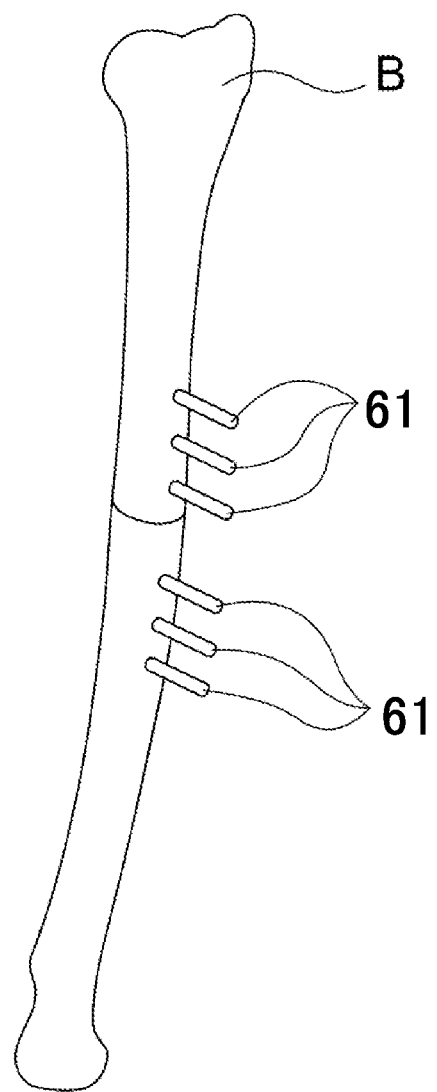
FIG. 20 is a drawing for explaining the operation procedure of the bone to be treated, showing the bone pieces moved to a target correction position.

The thrusting positions of the first rod are determine such that, when the bone pieces BP1 and BP2 produced by cutting the bone B to be treated along the cutting cross-section are moved to the target correction position to form the bone of the normal condition, the first rods thrust into the bone pieces BP1 and BP2 assume a predetermined positional relationship therebetween (an example is shown in FIG. 20 to be subsequently referred to). In other words, the first guide hole 15 guides, when the bone treatment assistance device 1 is attached to the bone B with the fitting surface fitted to the surface of the bone, and after the bone pieces cut and divided along the cutting cross-section are corrected into the positional relation under the normal condition, the first rod to be inserted in the bone, such that the first rod inserted in a bone piece assumes a predetermined positional relation with respect to another first rod inserted in the bone piece. The protrusions 151 to 156 of the respective first guide holes 15 are formed so as to protrude from the side face 11, in the direction that allows the first rod to be guided in the mentioned posture.

In this embodiment, the main body 11 includes four three first guide holes 15 for the bone piece BP1, and three first guide holes 15 for the bone piece BP2, to allow three first rods to be thrust into the bone piece BP1, and three first rods to be thrust into the bone piece BP2. However, the number of first guide holes 15 formed for the bone pieces BP1 and BP2 is not specifically limited.

Figure 5:
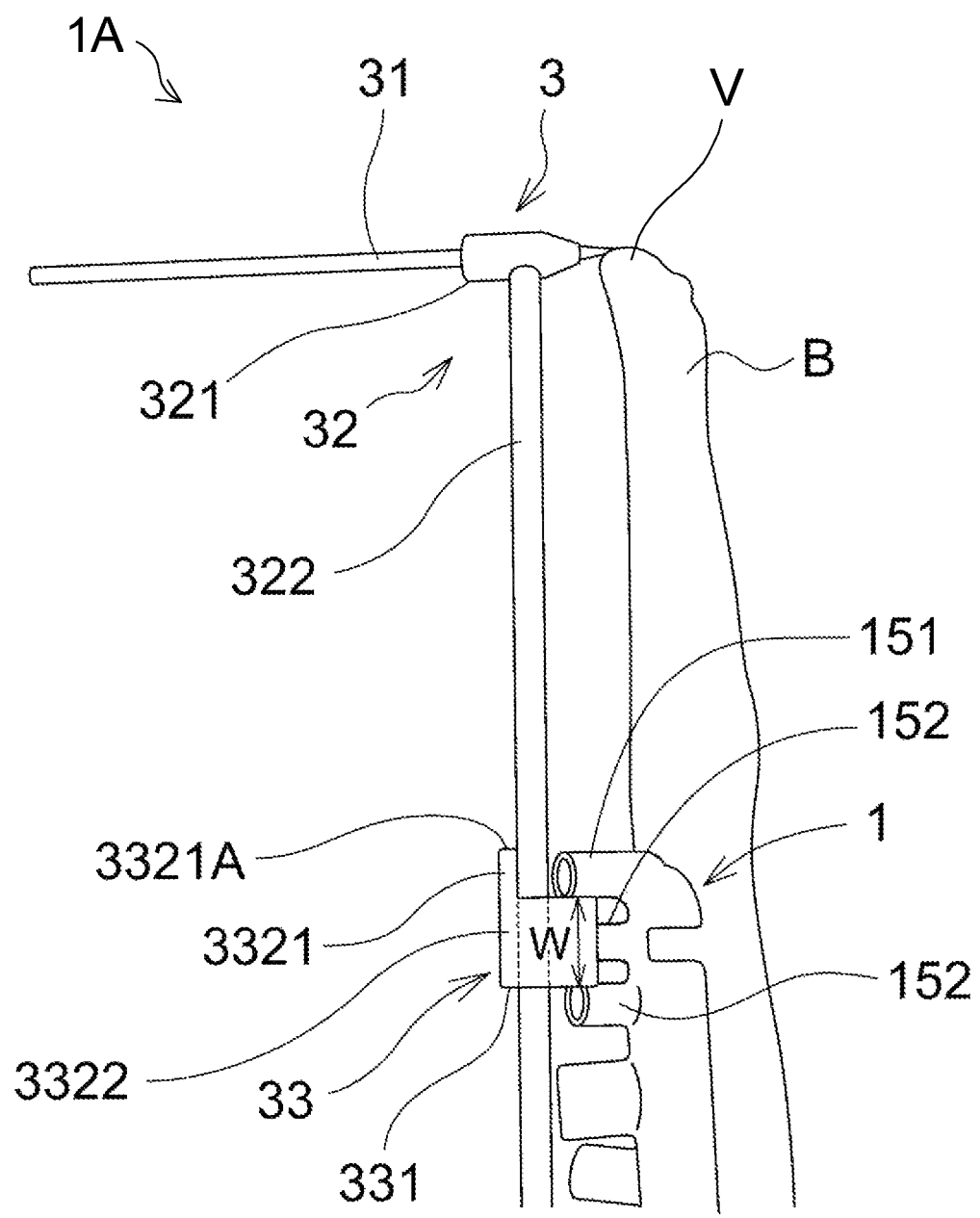
FIG. 5 is a drawing showing the attaching position confirmation device, attached to the bone treatment assistance device attached to the bone to be treated.

Referring to FIG. 4 and FIG. 5, the attaching position confirmation device 3 will be described. The attaching position confirmation device 3 includes a first rod 31, a rod support unit 32, and a second support member 33.

The first rod 31 is to be applied, via the tip portion thereof, to a feature point V, which is a predetermined specific portion, of the bone B.

The feature point V is a portion of the bone B designated in advance by the surgeon. The surgeon determines, before the operation, a portion of the bone B to which the tip portion of the first rod 31 is to be applied, as the feature point V. A portion of the bone B having a shape that can be easily recognized by the operator is selected as the feature point V. Regarding the upper limb region, for example, the tip portion of a styloid process, and medial epicondyle of humerus may be preferably selected as the feature point V. The feature point V generally refers to a point of a distinctive shape of the bone that every human has, for example, in anatomical terminology, the styloid process in the case of an ulna or rib, and the medial epicondyle in the case of a humerus. The feature point V does not represent a shape unique to an individual patient. A portion of a bone morphologically distinctive, and appropriate for use as a landmark of position information, is selected as the feature point V.

The feature point V is utilized by the surgeon to confirm that the bone treatment assistance device 1 is located at the intended position on the bone B to be treated, when the tip portion of the first rod 31 has reached and is indicating the feature point V.

The rod support unit 32 includes a rod support member 321 and an elongate member 322. The rod support member 321 includes a cylindrical through hole 325, formed so as to penetrate through the support member 321. The diameter of the through hole 325 is the same as, or slightly larger than that of the first rod 31.

The diameter of the first rod 31 is the same as, or slightly smaller than that of the through hole 325. The through hole 325 is formed so as to allow the first rod 31 to pass therethrough, when the first rod 31 is inserted. The rod support unit 32 supports the first rod 31 inserted through the through hole 325, with the tip portion of the first rod 31 exposed from the rod support member 321. In this state, the exposed tip portion of the first rod 31 can be applied to the feature point V of the bone B. Thus, the rod support member 321 supports the first rod 31 so as to be inserted or removed, in the posture where the tip portion is directed to the feature point V of the bone B.

An end portion 3211 of the rod support member 321, from which the tip portion of the first rod 31 is exposed, and opposed to the feature point V of the bone B, is formed in a tapered shape as shown in FIG. 4. The tapered shape of the end portion 3211 facilitates the surgeon to recognize the tip portion of the first rod 31 exposed from the rod support member 321.

The elongate member 322 has an elongate shape extending from the rod support member 321. The elongate member 322 is connected to the rod support member 321, and extends, for example, in a direction orthogonal to the longitudinal direction of the rod support member 321. The elongate member 322 includes a plurality of scales M provided along the extending direction. The plurality of scales M include scales M1 to M5, provided at regular intervals along the extending direction. The scales M1 to M5 are formed on the elongate member 322, for example by making notches. The number of scales is not specifically limited.

The second support member 33 supports the elongate member 322 of the rod support unit 32, so as to move in the extending direction. The second support member 33 includes a main body 331, for example having a rectangular block shape, and a support unit 332 that receives and supports the elongate member 322 of the rod support unit 32. The main body 331 of the rectangular block shape, is integrally formed with the support unit 332. The width W of the main body 331 corresponds to the distance between the outer edge of the protrusion 151 and that of the protrusion 153 of the bone treatment assistance device 1.

A side face 3311 of the main body 331 includes the opening of a recess 3312. The recess 3312 has the same size as the diameter of the protrusion 152 of the first guide hole 15, to allow the protrusion 152 to be fitted in the recess 3312. Accordingly, as shown in FIG. 5, the main body 331 can be fitted between the protrusion 151 and the protrusion 153, with the protrusion 152 fitted in the recess 3312. In this state, where the protrusion 152 is fitted in the recess 3312 and the main body 331 is fitted between the protrusions 151 and 153, the second support member 33 is fixed to the main body 11 of the bone treatment assistance device 1.

Further, the support unit 332 includes a projecting portion 3321 and a through hole 3322. The support unit 332 is provided on the side of the outer face 3313 of the main body 331. The projecting portion 3321 and the through hole 3322 extend in the direction of the width W. The main body 331 includes a through hole 3322 formed thereinside, so as to extend in the direction of the width W. The inner shape of the through hole 3322 is formed in the same size as the outer shape of the elongate member 322 of the rod support unit 32, to allow the elongate member 322 to be inserted so as to move in the direction of the width W.

The scales M1 to M5 provided on the elongate member 322 are formed so as to extend in the direction orthogonal to the extending direction, and parallel to an upper edge 3321A of the projecting portion 3321. When the elongate member 322 is passed through the through hole 3322 and moved in the extending direction, the upper edge 3321A can be aligned with one of the scales M1 to M5. In other words, the upper edge 3321A of the projecting portion 3321 of the support unit 332 indicates one of the scales M1 to M5.

The surgeon determines the feature point V before the operation, as the portion of the bone B to which the tip portion of the first rod 31 supported by the rod support member 321 is to be applied. The bone treatment assistance device 1 is attached to the bone B, with the fitting surface 12 fitted to the surface of the bone B. In the attaching position confirmation device 3, the second support member 33 is fixed to the main body 11 of the bone treatment assistance device 1 attached as above to the bone B, when the protrusion 152 is fitted in the recess 3312 and the main body 331 is fitted between the protrusions 151 and 153.

The elongate member 322 of the rod support unit 32 is passed through the through hole 3322 of the second support member 33, fixed as above to the bone treatment assistance device 1, thus to be supported by the second support member 33. When performing the operation, the surgeon moves the elongate member 322 with respect to the support unit 332, such that the tip portion of the first rod 31 supported by the rod support unit 32 indicates the feature point V, and adjusts the length by which the elongate member 322 is inserted in the second support member 33. As result of such adjustment, the upper edge 3321A of the projecting portion 3321 is made to indicate one of the scales M1 to M5.

In this embodiment, the bone pieces BP1 and BP2, to each of which the first rod has been thrust, are moved, so that the surgeon can decide that the bone pieces BP1 and BP2 are located at the target correction position with respect to each other, upon visually confirming that the first rod thrust into one of the bone pieces and the first rod thrust into the other bone piece are in a predetermined positional relation (further detail will subsequently follow).

Hereunder, the bone treatment assistance device manufacturing program employed for manufacturing the bone treatment assistance device 1 will be described. The bone treatment assistance device 1 is manufactured through a rapid prototyping method such as optical modelling, according to a stereoscopic three-dimensional model data generated and outputted by the bone treatment assistance device manufacturing program. The bone treatment assistance device manufacturing program is installed in an information processing device.

Figure 6:
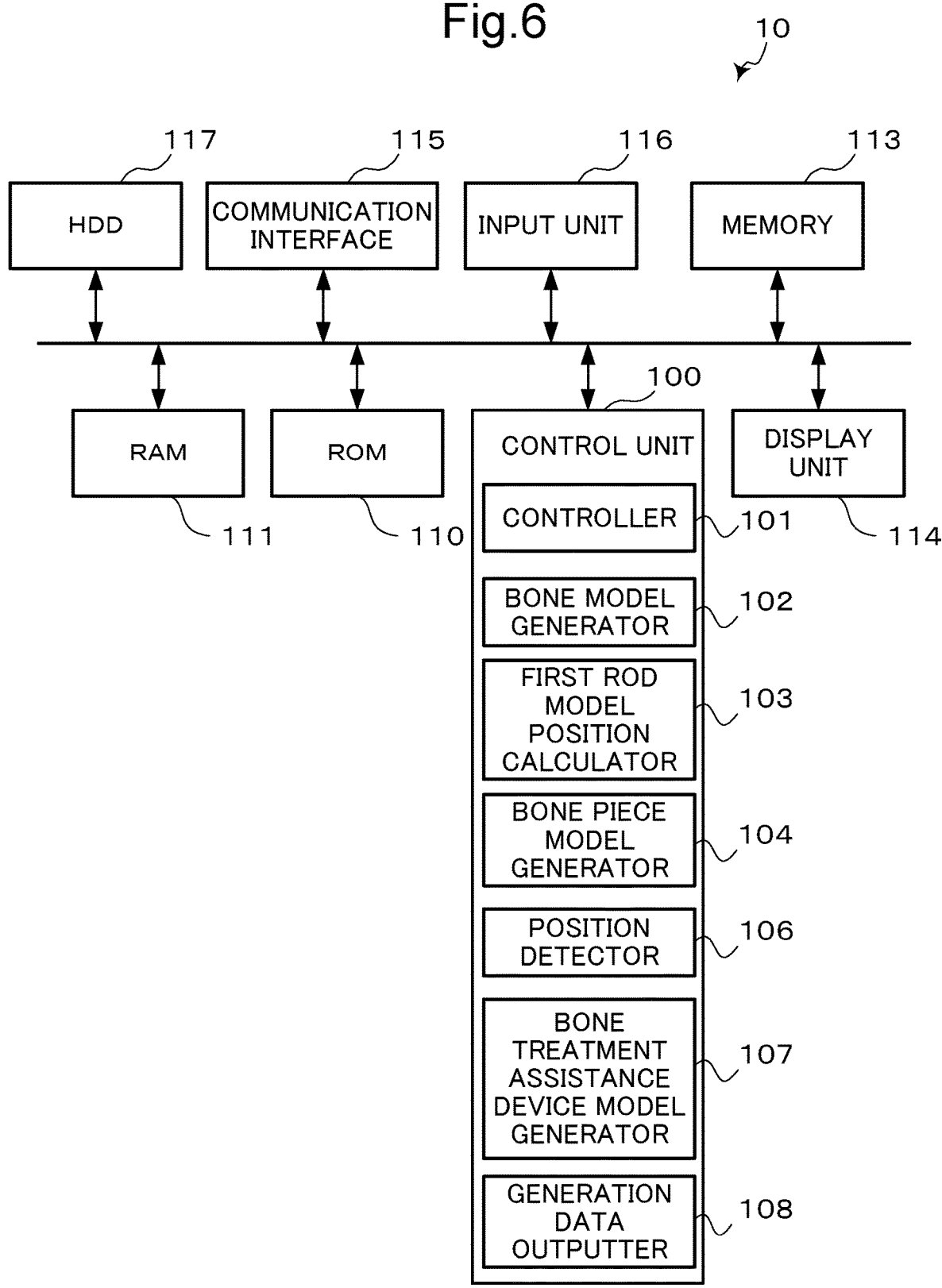
FIG. 6 is a block diagram showing a configuration of an information processing device with a manufacturing program of the bone treatment assistance device installed therein.

FIG. 6 is a block diagram showing a configuration of the information processing device with the bone treatment assistance device manufacturing program installed therein.

The information processing device 10 includes a control unit 100, a ROM 110, a RAM 111, a memory 113, a display unit 114, a communication interface 115, an input unit 116, and a HDD 117. These components are configured to transmit and receive data and signals between each other, through a CPU bus.

The control unit 100 includes a CPU or the like. The ROM 110 stores operation programs of basic functions of the information processing device 10. The RAM 111 is utilized as operating region for the control unit 100.

The memory 113 is a storage medium for storing data such as the stereoscopic three-dimensional model data for manufacturing the bone treatment assistance device 1, transmitted from an image pickup device.

HDD 117 is a storage region where the bone treatment assistance device manufacturing program is installed.

The control unit 100 includes a controller 101, a bone model generator 102, a first rod model position calculator 103, a bone piece model generator 104, a position detector 106, a bone treatment assistance device model generator 107, and a generation data outputter 108.

The control unit 100 acts, upon operating according to the bone treatment assistance device manufacturing program installed in the HDD 117, as the controller 101, the bone model generator 102, the first rod model position calculator 103, the bone piece model generator 104, the position detector 106, the bone treatment assistance device model generator 107, and the generation data outputter 108, and thus includes the mentioned components.

Alternatively, the controller 101, the bone model generator 102, the first rod model position calculator 103, the bone piece model generator 104, the position detector 106, the bone treatment assistance device model generator 107, and the generation data outputter 108 may each be constituted of a hardware circuit, instead of being realized through the operation according to the bone treatment assistance device manufacturing program. This also applies to other embodiments, unless otherwise specifically noted.

The controller 101 controls the overall operation of the information processing device 10, for example the displaying operation of the display unit 114.

The bone model generator 102 acquires the stereographic three-dimensional data of the bone B to be treated, from the image pickup device such as a CT scanner through the communication interface 115. The bone model generator 102 generates a three-dimensional bone model representing the bone B, on the basis of the acquired three-dimensional data. The bone model is a stereographic image represented by computer graphics.

The bone piece model generator 104 generates bone piece models by cutting the bone model along a cutting cross-section for correction specified with respect to the bone model. For example, the controller 101 causes the display unit 114 to display a graphic image representing the bone model and a graphic image representing a plurality of cutting cross-sections aligned in the longitudinal direction of the bone model and each inclined by a certain angle with respect to a longitudinal axis of the bone model. The certain angle is determined according to an instruction from the operator inputted through the input unit 116. The operator designates, out of the plurality of graphic images representing the cutting cross-section, a graphic image representing the cutting cross-section located at the desired position with respect to the bone model, through the input unit 116. When such designation is inputted, the bone piece model generator 104 acquires coordinate position information indicating the coordinate position where the cutting cross-section corresponding to the designated graphic image is displayed. The operator determines the cutting cross-section for the bone model, through the mentioned operation, so as to enable each of the bone piece models produced by cutting to move to the target correction position approximate to a target bone model representing the correction goal. The bone piece models have different shapes depending on the position and angle of the cutting cross-section along which the bone is cut.

The controller 101 causes the display unit 114 to display the bone piece models cut as above, and then to display the bone piece models with variation of positions on the graphics, according to the instruction from the operator inputted through the input unit 116. Accordingly, the operator can simulate whether the generated bone piece models can be moved to the target correction position, to thereby set the cutting cross-section to the most appropriate position.

The first rod model position calculator 103 acquires the position of the first rod models attached to each of the bone piece models located at the target correction position, and calculates, on the basis of the position of the first rod models, the position of the first rod models with respect to the corresponding bone piece model, taken when the bone piece models are moved to the position for constituting the bone model (uncorrected yet). For example, a plurality of first rod models are attached to each of the bone piece models located at the target correction position. Alternatively, a single piece of first rod model may be attached to each bone piece model. In the case where a plurality of first rod models are attached to each bone piece model, the first rod models attached to each bone piece model may be set parallel to each other. The first rod model refers to a stereographic image representing the shape of the first rod created by computer graphics. The three-dimensional data representing the first rod model is possessed by the position detector 106.

The bone treatment assistance device model generator 107 generates a bone treatment assistance device model, on the basis of basic image data representing the bone treatment assistance device, the bone model generated as above, the position of the cutting cross-section determined as above, and the calculated position of the first rod model. The bone treatment assistance device model is a three-dimensional image representing the bone treatment assistance device 1 by a graphic image. The bone treatment assistance device model includes a main body model corresponding to the main body 11 of the bone treatment assistance device 1, a fitting surface model corresponding to the fitting surface, a cutting slit model corresponding to the cutting slit 13, a first guide hole model representing the first guide hole located at the position of the first rod model so as to allow the first rod model to be inserted therethrough, and guide hole models representing the respective guide holes located at the calculated positions of the first rod models to allow the first rod models to be inserted therethrough.

The generation data outputter 108 outputs the three-dimensional data representing the bone treatment assistance device model generated by the bone treatment assistance device model generator 107 as three-dimensional data for manufacturing the bone treatment assistance device 1, for example to a USB memory, another information processing device, or an NC machine tool, through the communication interface 115. With the three-dimensional manufacturing data, the bone treatment assistance device or a tooling for manufacturing the bone treatment assistance device can be fabricated.

The position detector 106 detects a distance from the position of the feature point on the bone model to the bone treatment assistance device model whose portion indicating the fitting surface is attached to a position that fits to a surface shape of the bone model uncorrected yet, at a time when a rod support unit model supporting a feature point indication rod model being applied via the tip portion to the feature point V on the bone model is attached to the second support member model that is attached to the bone treatment assistance device model attached to the bone model.

Here, in this embodiment it will be assumed that the position detector 106 detects, as the mentioned distance, the scale indicated by the portion of the second support member model corresponding to the upper edge of the projecting portion, out of the plurality of scales provided at different positions on the elongate member model, along the direction in which the elongate member model extends from the rod support unit model in the elongate shape.

The display unit 114 is constituted of a liquid crystal display (LCD) or the like, and displays, under the control of the controller 101, the aforementioned images, the content of various data, and user guides for operating the information processing device 10.

The communication interface 115 includes a USB interface for example, and outputs the bone treatment assistance device manufacturing data to, for example, an external memory connected to the information processing device 10, another information processing device, or an NC machine tool. The communication interface 115 also serves as an interface for acquiring the three-dimensional data from the image pickup device such as a CT scanner, or the USB memory.

The input unit 116 is constituted of a keyboard and a mouse pointer provided in the information processing device 10, and a touch panel device provided in the display screen of the display unit 114, and used by the operator to input various instructions.

Figure 7:
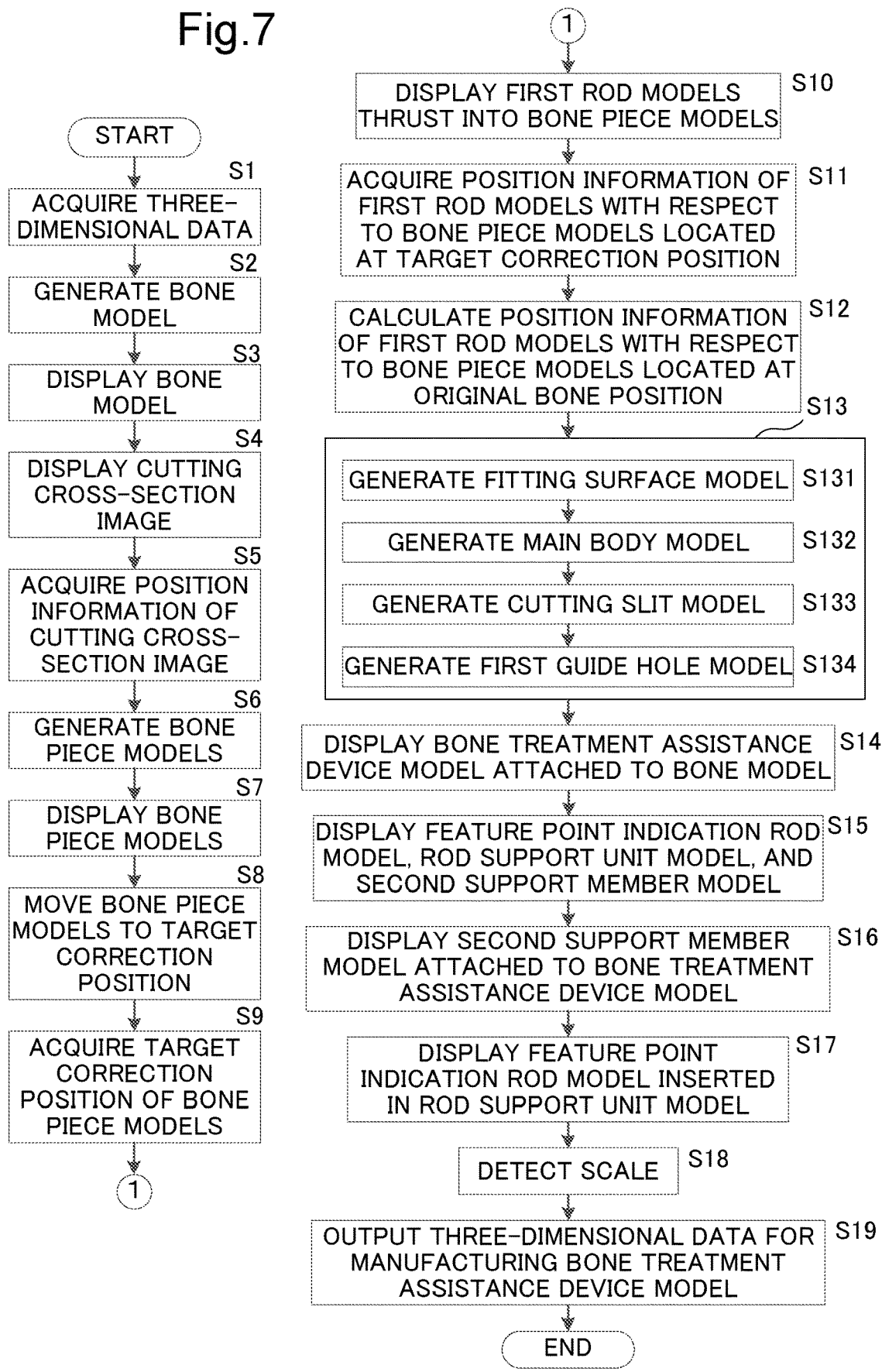
FIG. 7 is a flowchart showing a process performed by the information processing device to generate manufacturing data of the bone treatment assistance device.

Hereunder, description will be given on a method of generating the bone treatment assistance device manufacturing data to be performed by the information processing device 10, having the bone treatment assistance device manufacturing program installed therein. FIG. 7 is a flowchart showing a process performed by the information processing device 10 to generate the bone treatment assistance device manufacturing data.

First, the bone B to be treated in the patient to undergo the corrective operation is shot by an image pickup device such as a CT scanner or MRI apparatus. In the case of CT scanning, the image pickup device acquires three-dimensional data composed of position information (in an X-direction and Y-direction) on the tomographic image and sets of images shot at different positions in the height direction of the patient (defined as Z-direction), obtained through the imaging. In addition, a normal portion of the patient's bone (for example, a portion of the bone on the side of the tendon, i.e., a portion having the shape to which the bone to be treated is to be corrected) is also shot by the image pickup device to acquire the three-dimensional data.

In the information processing device 10, the bone treatment assistance device manufacturing program is activated and the control unit 100 is made to act as the functional units from the bone model generator 102 to the generation data outputter 108. The operator inputs the three-dimensional data of the bone B to be treated and the three-dimensional data of the normal portion of the bone acquired through the image pickup device to the information processing device 10 through the communication interface 115, via a USB memory or USB connection. The bone model generator 102 acquires the three-dimensional data from the image pickup device through the communication interface 115 (S1).

The bone model generator 102 generates a bone model BM representing the bone B, according to the three-dimensional data of the bone B to be treated, acquired as above (S2).

Figure 8:
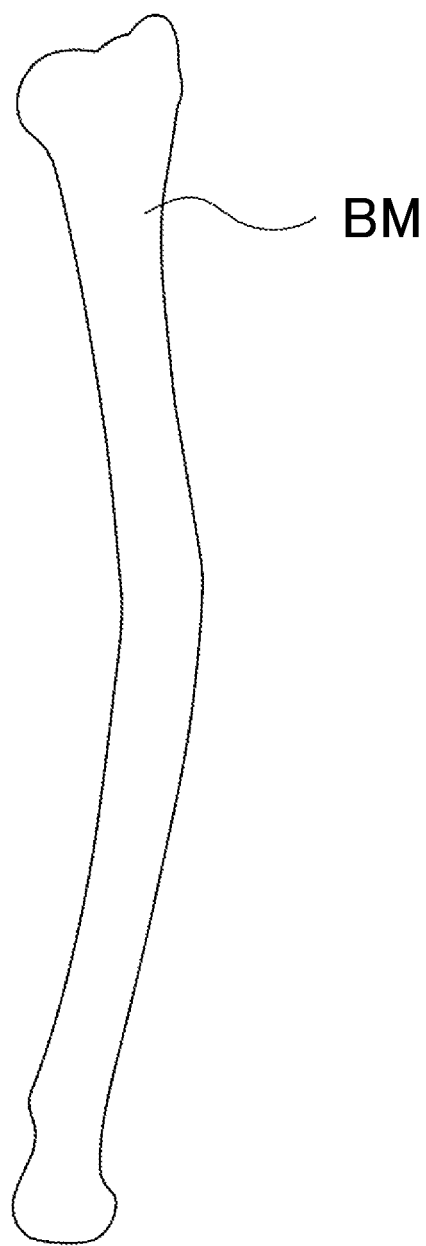
FIG. 8 illustrates an example of a display screen showing a generated bone model.

The controller 101 of the information processing device 10 causes the display unit 114 to display the bone model BM generated as above (S3). An example of the screen displayed by the display unit 114 is shown in FIG. 8. The controller 101 causes the bone model BM to be displayed in different angles and positions according to the instruction from the operator inputted through the input unit 116.

Figure 9:
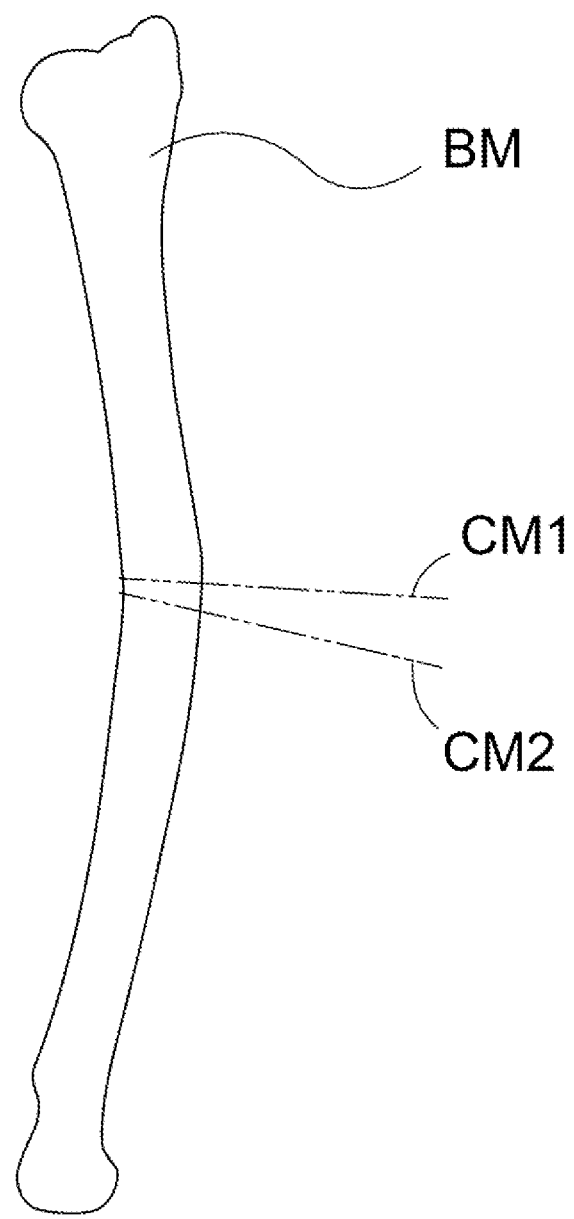
FIG. 9 illustrates an example of the display screen showing the bone model and cutting cross-sections.

Then the controller 101 causes the display unit 114 to further display, as shown in FIG. 9, a plurality of cutting cross-section images CM1 and CM2 representing the cutting cross-sections, according to the instruction from the operator inputted through the input unit 116, in addition to the first rod model LM1, the bone model BM, and the target bone model TBM (S4). According to the operation made by the operator through the input unit 116, the controller 101 causes the cutting cross-section images CM1 and CM2 to be displayed at desired positions, with respect to the bone model BM. When the operator inputs the instruction to acquire the position information through the input unit 116, after the cutting cross-section images CM1 and CM2 are displayed at the position designated by the operator as above, the bone model generator 102 acquires the coordinate position information of the cutting cross-section images CM1 and CM2 located at the designated position with respect to the bone model BM (see FIG. 9), as the respective positions of the cutting cross-section images CM1 and CM2 (S5).

Then, the bone piece model generator 104 generates divided images of the bone model BM cut at the position indicated by the plurality of cutting cross-section images CM, as bone piece models BPM1 and BPM2 (S6).

Figure 10:
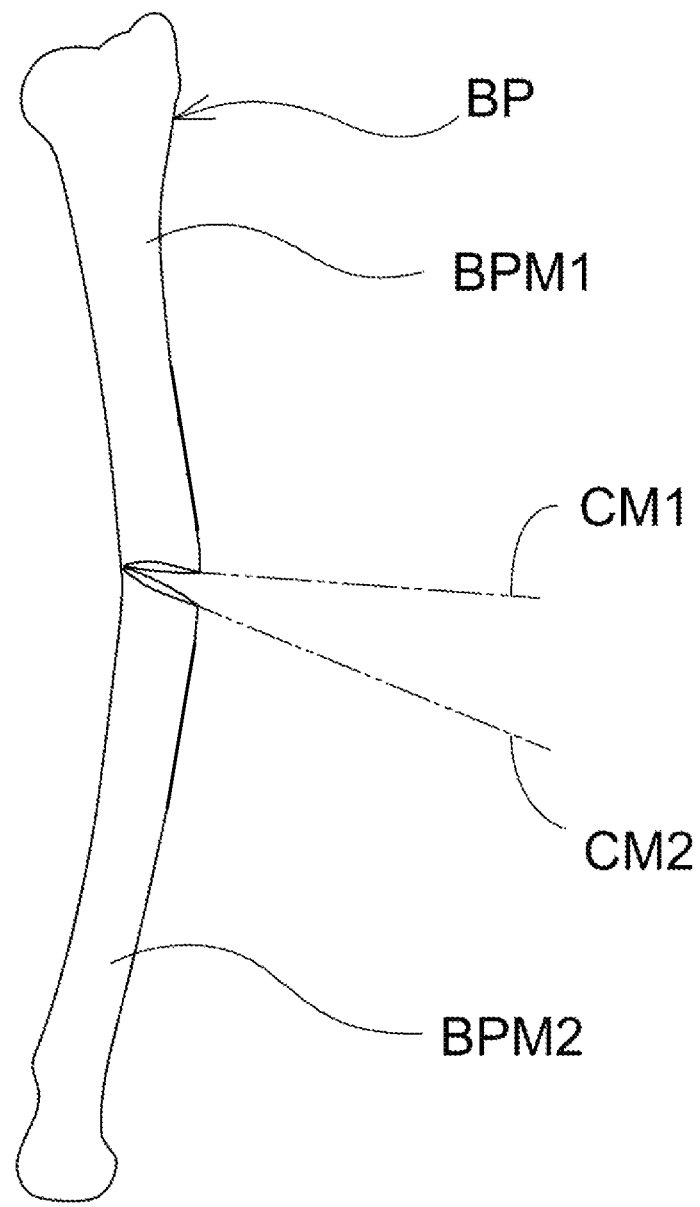
FIG. 10 illustrates an example of the display screen showing bone piece models in place of the bone model.

The controller 101 causes the display unit 114 to further display the bone piece models BPM1 and BPM2 generated as above, in place of the bone model BM, as shown in FIG. 10 (S7). Here, FIG. 10 illustrates an example of the image displayed by the controller 101, where the bone has been cut along the cutting cross-section images CM1 and CM2, and the portion of the bone located between the cutting cross-section images CM1 and CM2 has been removed.

Figure 11:
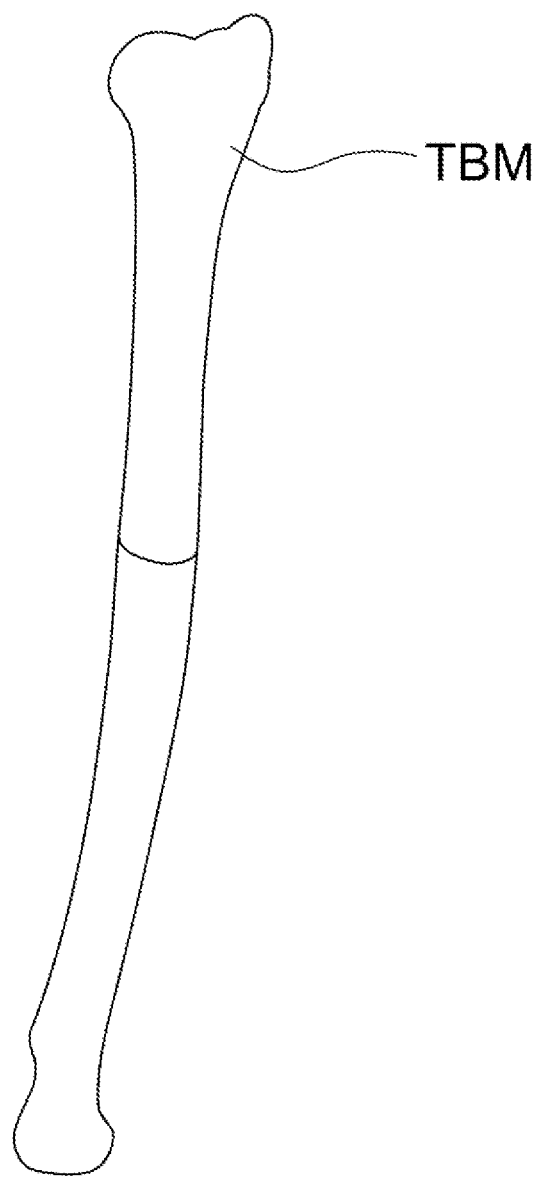
FIG. 11 illustrates an example of the display screen showing the bone piece models located at a target correction position.

The controller 101 then displays the bone piece models BPM1 and BPM2, in a different display angle and different display position, according to the instruction from the operator inputted through the input unit 116. The controller 101 moves the combination of the bone piece models BPM1 and BPM2 to the position corresponding to the target bone model TBM representing the target shape of the correction, as shown in FIG. 11, according to the instruction from the operator inputted through the input unit 116 (S8), and causes the display unit 114 to display such a state.

When the operator inputs the instruction to acquire the position information at this point, the bone treatment assistance device model generator 107 acquires the coordinate position information of each of the bone piece models BPM1 and BPM2, on the assumption that the coordinate positions in the graphic displaying the bone piece models BPM1 and BPM2 at this time point correspond to the target correction positions to which the bone piece models BPM1 and BPM2 are to be respectively moved (S9). However, the foregoing acquisition method of the target correction position is merely exemplary, and any different method may be adopted to acquire the target correction position.

Figure 12:
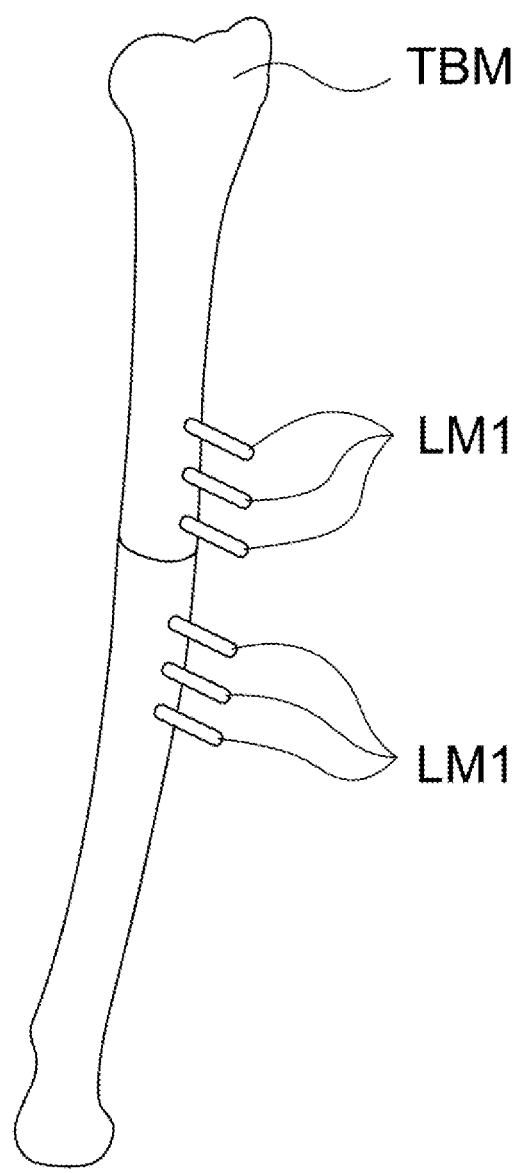
FIG. 12 illustrates an example of the display screen showing a plurality of first rod models thrust into the bone piece models.

At this point, for example the controller 101 causes the display unit 114 to display the first rod model LM1, according to the instruction from the operator inputted through the input unit 116 (in this example, three first rod models on the bone piece model BPM1 and three first rod models on BPM2). The controller 101 causes the first rod models LM1 at different positions on the graphic, according to the instruction from the operator. The controller 101 displays the first rod model LM1 at a position desired by the operator with respect to the bone piece models BPM1 and BPM2, for example in a state where the first rod models LM1 are thrust (inserted) into the bone piece model BPM1 or BPM2, according to the instruction from the operator (S10). The controller 101 keeps the display of the image representing the bone piece model with the first rod models thrust thereto. As shown in FIG. 12 for example, the image representing a plurality of first rod models LM1 thrust into each of the bone piece models BPM1 and BPM2 is displayed. For example, the operator may operate the input unit 116, to align the plurality of first rod models LM1 parallel to each other and thrust them into the bone piece models BPM1 and BPM2, as shown in FIG. 12, and to cause the controller 101 to display the mentioned state.

Upon receipt of the instruction to acquire the position information from the operator, while the first rod models LM1 thrust into each of the bone piece models BPM1 and BPM2 are displayed, the position detector 106 acquires the coordinate position information of the first rod models LM1, on the assumption that the coordinate positions of the respective first rod models LM1 shown on the graphic at this point correspond to the positions of the first rod models LM1 with respect to the bone piece models BPM1 and BPM2 located at the target correction position (S11).

The position detector 106 then calculates the coordinate position information indicating the positions of the first rod models LM1 with respect to the bone piece models BPM1 and BPM2, determined when the first rod models LM1 have moved from the position with respect to the bone piece models BPM1 and BPM2 located at the target correction position, to the position where the bone piece models BPM1 and BPM2 constitute the aforementioned bone model BM (S12).

Then the bone treatment assistance device model generator 107 generates the bone treatment assistance device model (S13). At S13, first the bone treatment assistance device model generator 107 generates a fitting surface model representing the shape of the fitting surface that fits the surface shape of the bone model BM, utilizing the three-dimensional data of the bone model BM uncorrected yet (S131).

The bone treatment assistance device model generator 107 also generates a main body model including the fitting surface model and corresponding to the main body 11 of the bone treatment assistance device 1, according to the instruction from the operator (S132).

Then the bone treatment assistance device model generator 107 generates a cutting slit model representing the cutting slit having a predetermined thickness, width, and length in the main body model, at the position and angle indicated by the position information of the cutting cross-section acquired at S5 (S133). In this process, the bone treatment assistance device model generator 107 also generates a support portion having a predetermined thickness, on an outer side of the slit model.

Further, the bone treatment assistance device model generator 107 generates, utilizing the position information of the first rod model acquired at S12, a guide hole model representing the guide hole through which the first rod model located at the corresponding position is to be inserted, in the main body model (S134). For example, the bone treatment assistance device model generator 107 generates the guide hole model having the same or a slightly larger diameter than the first rod model and a predetermined length, at the position on the main body model indicated by the position information of the first rod model acquired at S12. The bone treatment assistance device model generator 107 generates, as the guide hole model, a model including the hole having the mentioned diameter, and a support portion formed around the hole in a predetermined thickness.

Through the mentioned process, the bone treatment assistance device model generator 107 generates a bone treatment assistance device model M representing the bone treatment assistance device 1 including the fitting surface, the cutting slit 13, and the first guide hole 15 formed in the main body 11, as shown in FIG. 1 and FIG. 2.

Figure 13:
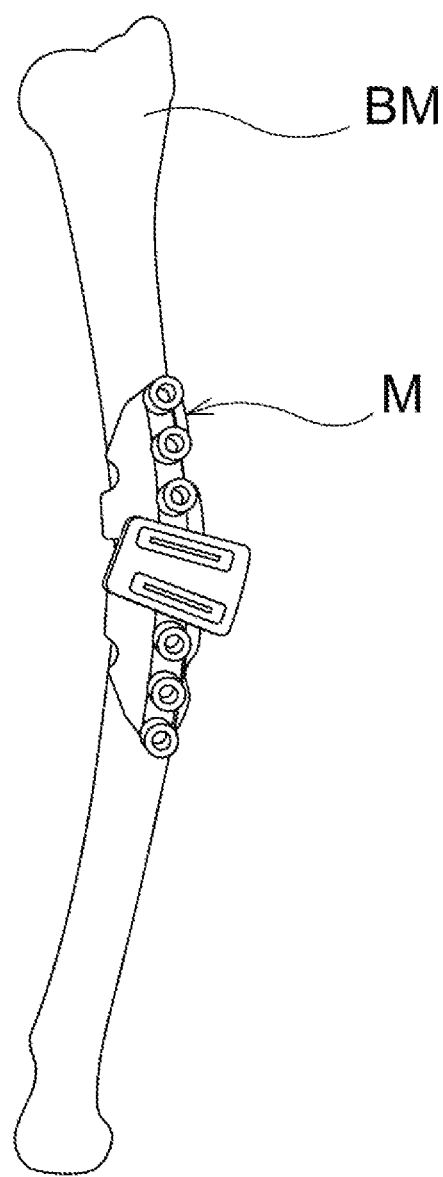
FIG. 13 illustrates an example of the display screen showing the bone treatment assistance device model attached to the bone model.

Then the controller 101 locates the bone treatment assistance device model M at the position where the portion corresponding to the fitting surface 12 fits the surface shape of the bone model BM uncorrected yet, according to the instruction from the operator inputted through the input unit 116, and causes the display unit 114 to display the bone treatment assistance device model M attached to the bone model BM (S14). An example of the display screen of the display unit 114 that appears at this point is shown in FIG. 13.

Further, upon receipt of the instruction to display the attaching position confirmation device 3 from the operator through the input unit 116, the controller 101 causes the display unit 114 to display a feature point indication rod model 31M, a rod support unit model 32M, and a second support member model 33M, respectively representing the feature point indication rod 31, the rod support unit 32, and the second support member 33 (S15).

Figure 14:
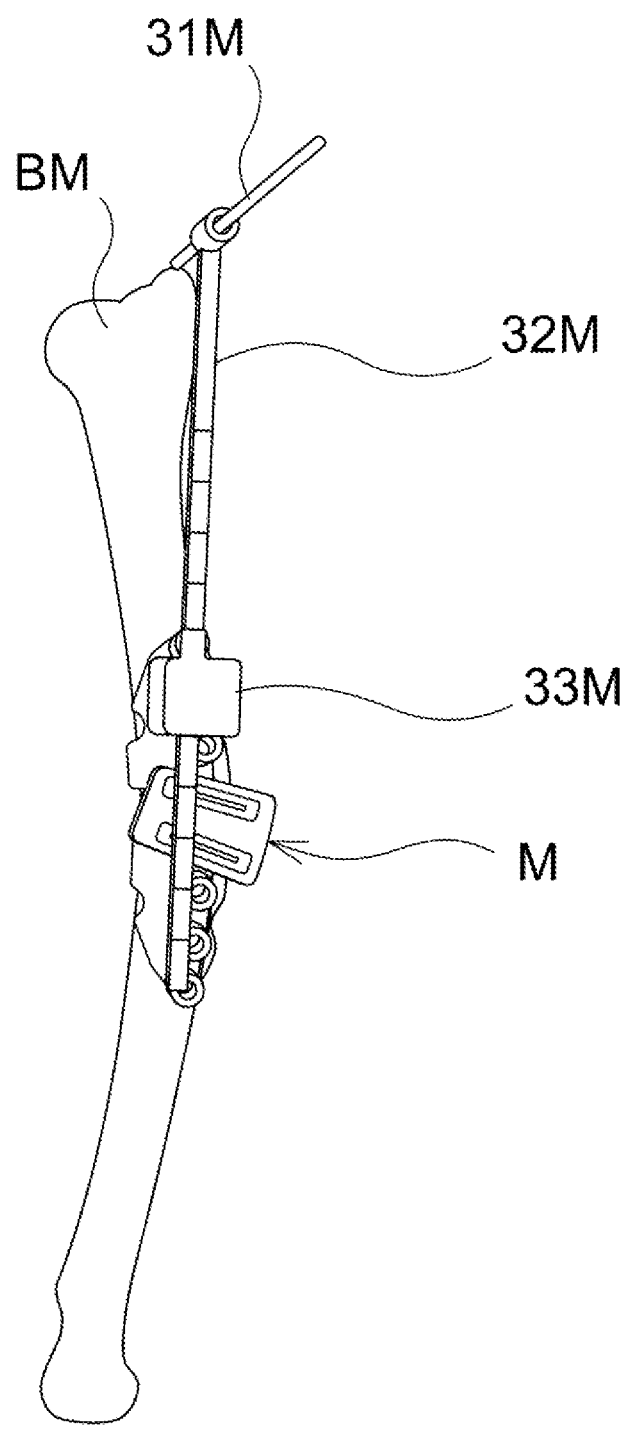
FIG. 14 illustrates an example of the display screen showing the attaching position confirmation device model attached to the bone treatment assistance device model.

The controller 101 causes the display unit 114 to display, according to the instruction from the operator inputted through the input unit 116, the second support member model 33M, such that the image of the portion thereof corresponding to the recess 3312 agrees with the position on the main body 11 of the bone treatment assistance device model M, where the image of the protrusion 152 is displayed, as shown in FIG. 14 (S16).

The controller 101 further causes the display unit 114 to display, according to the instruction from the operator inputted through the input unit 116, the feature point indication rod model 31M and the rod support unit model 32M at different positions. In this example, the controller 101 causes the display unit 114 to display, according to the instruction from the operator inputted through the input unit 116, a state where, as shown in FIG. 14, the feature point indication rod model 31M is passed through the rod support unit model 32M, and the tip portion of the feature point indication rod model 31M is exposed from the rod support unit model 32M (S17).

From the mentioned state, the controller 101 further causes the display unit 114 to display, according to the instruction from the operator inputted through the input unit 116, the rod support unit model 32M and the feature point indication rod model 31M which have been moved in the direction in which the image of the portion corresponding to the elongate member extends, to the position where the tip portion of the feature point indication rod model 31M, passed through the rod support unit model 32M, indicates the image representing the portion of the bone model BM corresponding to the feature point V.

When the instruction to acquire the position information is inputted by the operator through the input unit 116 at this point, the position detector 106 detects the scale indicated by the image of the portion of the second support member model 33M corresponding to the upper edge 2321A, out of the plurality of scales provided in the image of the portion corresponding to the elongate member of the rod support unit model 32M displayed while supporting the feature point indication rod model 31M (information on which of the scales M1 to M5 is indicated), and acquires the detection result as the distance between the feature point V of the bone model M and the bone treatment assistance device model M, the portion of which corresponding to the fitting surface 12 is attached to the bone model BM uncorrected yet, so as to fit the surface shape thereof (S18). Here, the position detector 106 may directly detect the information indicating the mentioned distance, instead of detecting the indicated scale (S18).

Alternatively, the operator may visually confirm the scale indicated by the image of the portion of the second support member model 33M corresponding to the upper edge 3321A when the mentioned state where the tip portion of the feature point indication rod model 31M, passed through the rod support unit model 32M, is indicating the image representing the portion corresponding to the feature point V, is displayed by the controller 101 on the display unit 114, and memorize the confirmed scale.

Then the generation data outputter 108 outputs, according to the instruction from the operator, the three-dimensional manufacturing data representing the bone treatment assistance device model generated by the bone treatment assistance device model generator 107 through the process from S131 to S134, for example to a USB memory, another information processing device, or an NC machine tool, through the communication interface 115 (S19).

Thereafter, the operator causes the NC machine tool to form the bone treatment assistance device 1 shown in FIG. 1, or forms the bone treatment assistance device 1 and the block 2 through a rapid prototyping method such as optical modelling. Alternatively, the operator may form the bone treatment assistance device 1 through a resin molding process using a tooling formed according to the three-dimensional data.

For example, the operator may form the bone treatment assistance device 1 by processing a material (e.g., metal, plastic, or ceramic) through a desired molding method such as optical modelling, on the basis of the three-dimensional manufacturing data. The optical modelling refers to a technique of curing a liquid-phase UV-curable resin (liquid that solidifies by reacting to UV light) with UV laser of an optical modelling apparatus and stacking the cured resin, thereby forming a three-dimensional object substantially equal to the 3D data, in a short time.

Through the foregoing method of manufacturing the bone treatment assistance device, the custom-made bone treatment assistance device 1 that fits the patient and his/her bone can be easily obtained, and optimum bone correction suitable to each of different patients can be performed.

Hereunder, an operation procedure for a bone to be treated utilizing the osteotomy assistance kit 1A, including the bone treatment assistance device 1 formed as above, will be described.

(1) First, the diseased part of the patient is incised so as to expose the portion to be cut, of the bone to be treated.

Figure 15:
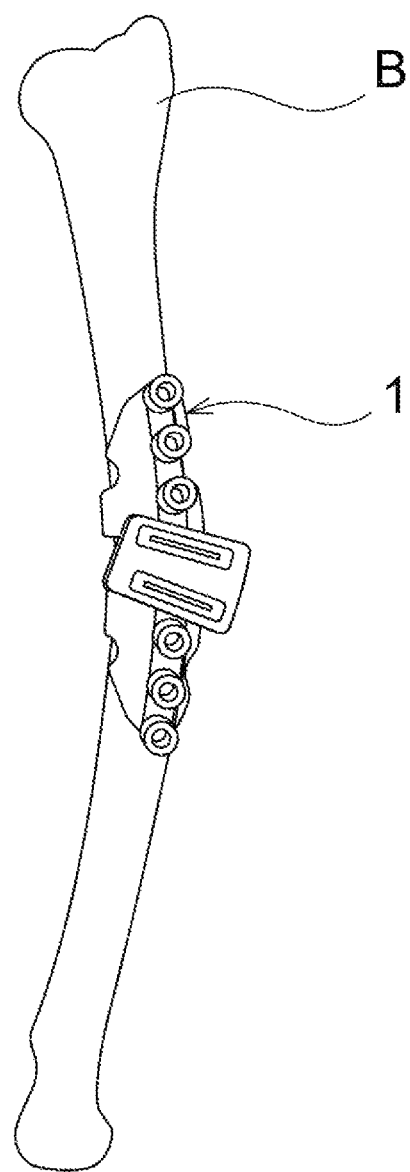
FIG. 15 is a drawing for explaining an operation procedure of a bone to be treated, showing the bone treatment assistance device set in close contact with the bone to be treated, with the fitting surface fitted to an appropriate position.

(2) Then the bone treatment assistance device 1 is brought into close contact with the bone B to be treated, with the fitting surface fitted to an appropriate position on the surface of the bone B, as shown in FIG. 15. By doing so, the bone treatment assistance device 1 is attached to the surface of the bone B to be treated, at the target position that accords with the cutting cross-section.

Figure 16:
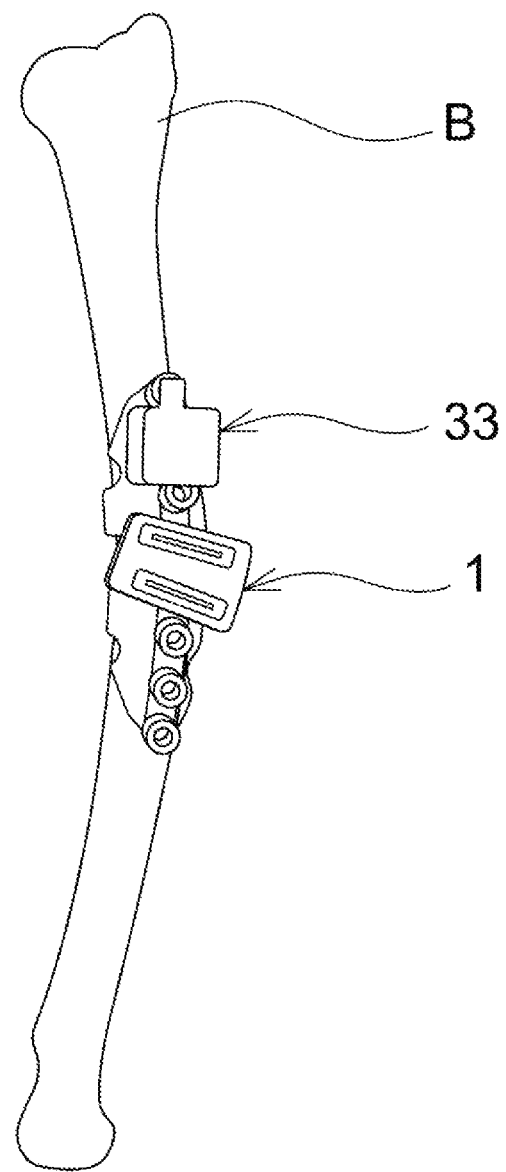
FIG. 16 is a drawing for explaining an operation procedure of the bone to be treated, illustrating an example of the display screen showing a second support member attached to the bone treatment assistance device model.

The surgeon then attaches the second support member 33 of the attaching position confirmation device 3 to the bone treatment assistance device 1, by fitting the protrusion 152 provided on the main body 11 of the bone treatment assistance device 1 in the recess 3312, and fitting the main body 331 between the protrusions 151 and 153, as shown in FIG. 16.

The surgeon inserts the feature point indication rod 31 through the rod support member 321 of the rod support unit 32 so as to expose the tip portion of the feature point indication rod 31 from the rod support unit 32, so that the rod support member 321 supports the feature point indication rod 31.

Figure 17:
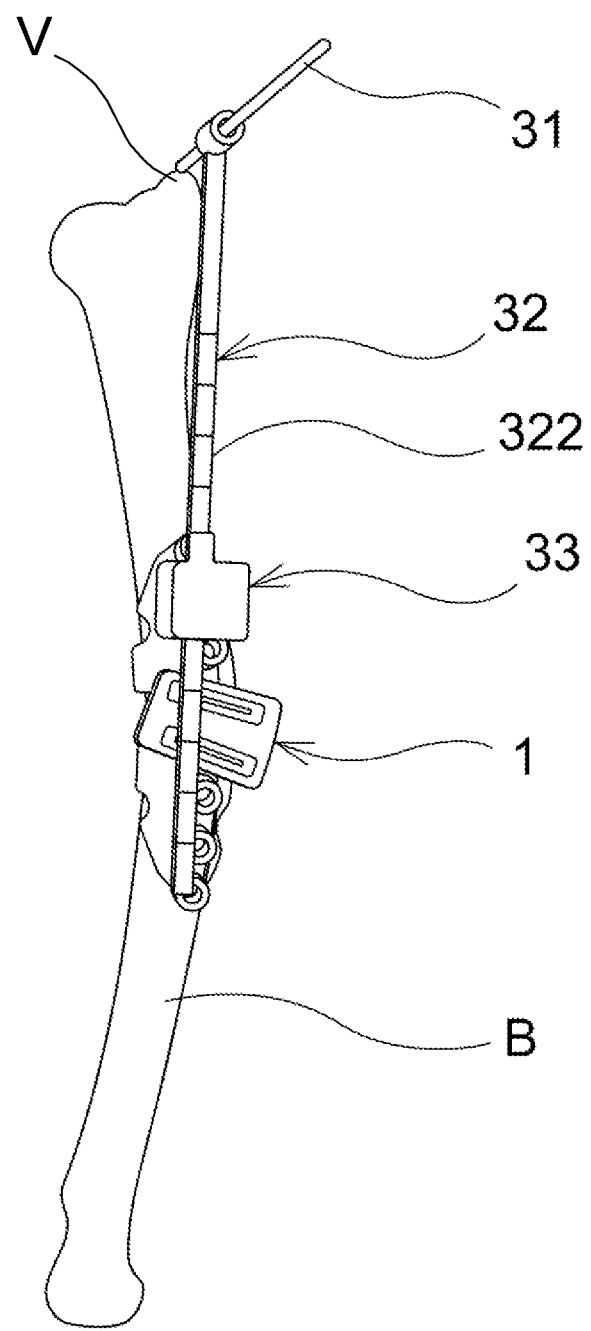
FIG. 17 is a drawing for explaining an operation procedure of the bone to be treated, illustrating an example of the display screen showing the attaching position confirmation device model attached to the bone treatment assistance device model.

Further, the surgeon inserts the distal end of the elongate member 322, a part of the rod support member 321 supporting the feature point indication rod 31, in the through hole 3322 of the second support member 33 attached to the bone treatment assistance device 1, as shown in FIG. 17. Accordingly, the rod support unit 32 supporting the feature point indication rod 31 is retained by the second support member 33.

When the surgeon moves the rod support unit 32 with respect to the second support member 33 in the longitudinal direction of the elongate member 322, with the rod support unit 32 supporting the feature point indication rod 31 retained by the second support member 33, the feature point indication rod 31 and the rod support unit 32 are moved to the position where the tip portion of the feature point indication rod 31 exposed from the rod support unit 32 indicates the feature point V of the bone B.

After the mentioned movement, the surgeon checks whether one of the scales M1 to M5 on the elongate member 322, indicated by the upper edge 3321A of the second support member 33 at this point, is the same as the scale indicated by the information acquired at S18 as a distance, in other words the information on which of the scales M1 to M5 is indicated. In the case where, as mentioned above, the operator visually confirmed and memorized the scale indicated by the image of the portion of the second support member model 33M corresponding to the upper edge 3321A, according to the display on the display unit 114, the surgeon may check whether the memorized scale and the scale indicated during the operation are the same.

In the case where the surgeon confirms at this point that the scale on the elongate member 322 indicated by the upper edge 3321A and the scale indicated by the position information acquired at S18 are the same, it can be assumed that the tip portion of the feature point indication rod 31 is indicating the feature point V of the bone B at the accurate position as intended.

In contrast, when the scale on the elongate member 322 indicated by the upper edge 3321A differs from the scale indicated by the position information acquired at S19 this point, the surgeon moves the bone treatment assistance device 1 with respect to the bone treatment assistance device 1, to the position where the scale on the elongate member 322 indicated by the upper edge 3321A accords with the scale indicated by the position information acquired at S19. Accordingly, the bone treatment assistance device 1 can be accurately attached to the target position on the bone B. Thereafter, the surgeon removes the attaching position confirmation device 3 from the bone treatment assistance device 1.

Figure 18:
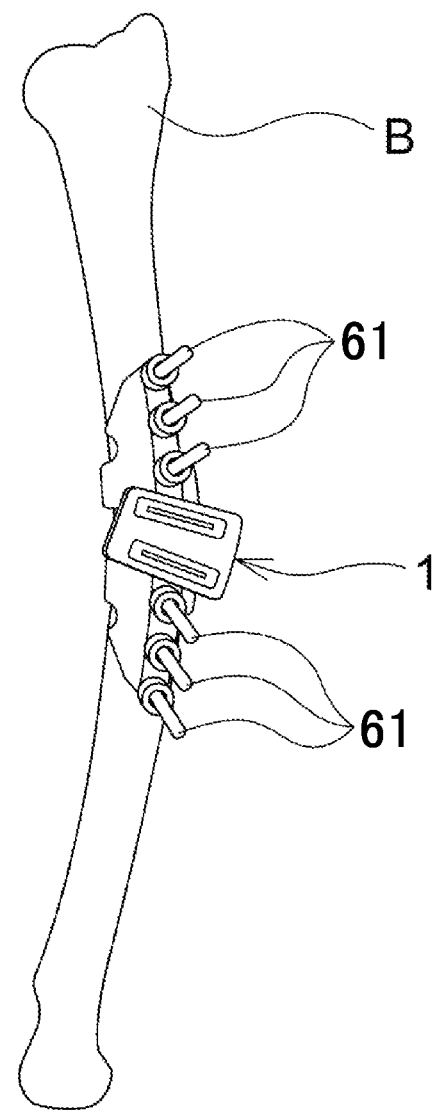
FIG. 18 is a drawing for explaining the operation procedure of the bone to be treated, showing first rods respectively inserted through first guide holes of the bone treatment assistance device, and thrust into the bone to be treated.

(3) The surgeon inserts the first rods 61 in the first guide holes 15 (protrusions 151 to 156) of the bone treatment assistance device 1 attached as above to the bone B, and thrusts the first rods 61 into the bone B to be treated, as shown in FIG. 18. The surgeon inserts the first rods 61 in the bone treatment assistance device 1, to such a depth that allows the first rods 61 to be fixed in the bone B. To do so, the surgeon may insert, for example, the tip portion of an electric drill in the first guide holes 15 (protrusions 151 to 156) in advance, to form holes for thrusting the first rod 31 in the bone B, at the angle and position guided by the first guide holes 15 (protrusions 151 to 156). In this embodiment, three first rods 61 are inserted at the positions corresponding to one of the bone pieces obtained by cutting the bone B to be treated, and three first rods 61 are inserted at the positions corresponding to the other bone piece.

(4) Then the surgeon inserts a cutting jig such as an electric saw in the cutting slits 131 and 132, and activates the cutting jig to thereby cut and divide the bone B. In the case where the first rod 31 is located at a position that interferes with the cutting operation, the first rod 31 may be removed from the bone B and the bone treatment assistance device 1 before the cutting, and the removed first rod 31 may be again inserted after the cutting, in the hole formed in the bone B by the thrusting of (3).

Figure 19:
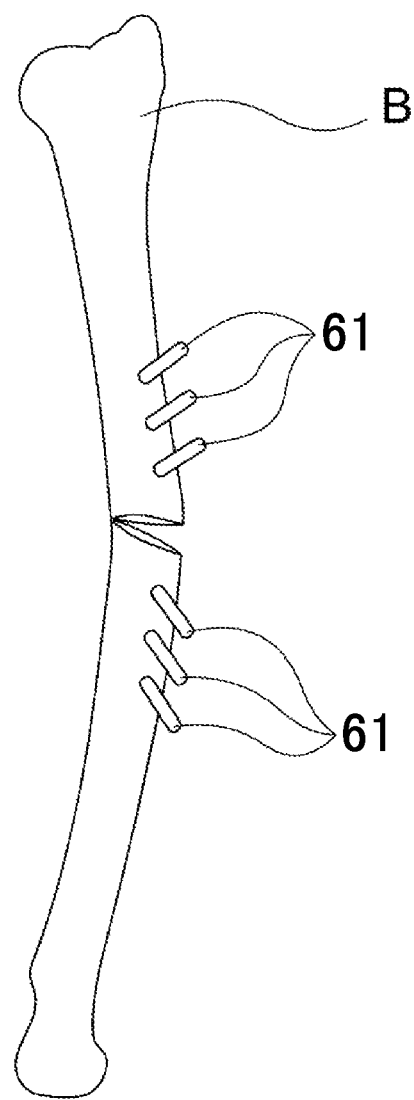
FIG. 19 is a drawing for explaining the operation procedure of the bone to be treated, showing the first rod thrust into the bone pieces.

(5) After the cutting operation, the bone treatment assistance device 1 is removed from the bone B leaving the first rod 31, as shown in FIG. 19. In this embodiment, at this point the bone B to be treated is divided into the bone pieces BP1 and BP2, each of which have the first rod 32 thrust thereto.

(6) The surgeon then moves the bone pieces BP1 and BP2 to the predetermined target correction position by visual measurement (see FIG. 20). Thereafter, the surgeon can confirm that the bone pieces BP1 and BP2 have moved to the target correction position, by visually confirming that, as shown in FIG. 20, the first rods 61 thrust into the bone pieces BP1 and BP2 are in the positional relation acquired at S11 (the first rods 61 being aligned parallel to each other).

Then the surgeon removes the first rods 61 from the bone pieces BP1 and BP2, and combines and fixes the bone pieces BP1 and BP2 set to the target correction position, using a non-illustrated block. Through the mentioned process, the relative positional relation between the bone pieces BP1 and BP2 is corrected to the positional relation according to the target correction position.

To combine the bone pieces BP1 and BP2, any desired method known in the art may be employed. The bone pieces may be combined with an internal fixing material such as a plate, a screw, a wire, or an intramedullary nail, and the gap, which is a defective part of bone, may be filled with calcium phosphate or a grafted bone. To fill the gap, for example, a biocompatible material such as calcium phosphate (e.g., hydroxyapatite), βTCP, or calcium phosphate paste may be employed. Alternatively, bone graft may be adopted for the defective part of bone.

After the bone pieces BP1 and BP2 are combined, it is desirable to maintain the combined state for a long period of time. This is because the corrected state is maintained so as to assure the effectiveness of the correction.

With the bone treatment assistance device 1 according to this embodiment, the bone can be cut, in the corrective bone cutting operation, along a proper cutting cross-section calculated in advance through computer simulation, and the bone pieces produced after the cutting can be easily moved to a proper target correction position determined through computer simulation. Therefore, the corrective bone cutting operation can be securely and easily performed, without depending on the experience, proficiency or skill of the surgeon as in conventional operations.

The arrangement according to this embodiment eliminates the need to thrust the rod into the feature point V of the bone B, merely to check whether the bone treatment assistance device 1 is attached to the target position on the bone B to be treated, when performing the operation, thereby exempting the bone from the unnecessary burden. It is no longer necessary to take the trouble of thrusting the rod into the feature point V of the bone B, to check whether the bone treatment assistance device 1 is attached to the target position on the bone B. Further, the arrangement according to this embodiment allows the surgeon to objectively recognize, on the basis of the scale on the elongate member 322 indicated by the upper edge 3321A of the second support member 33, whether the bone treatment assistance device 1 is accurately attached to the target position on the bone B to be treated, or to what extent the bone treatment assistance device 1 is deviated.

Consequently, the configuration according to the foregoing embodiment makes it possible to recognize how accurately the bone treatment assistance device is attached to the target position on the bone to be treated, with a reduced impact on the bone, and with reduced workload.

The present invention may be modified in various manners, without limitation to the foregoing embodiment.

The configurations and operations described in the foregoing embodiments with reference to FIG. 1 through FIG. 20 are merely exemplary, and the configurations and operations of the present invention are in no way limited to the above.

Although the bone of the limb is taken up as object of the treatment in the foregoing embodiments, the present invention is applicable to any chosen bone without limitation to the limb bone. In the case of a human body, all of the approximately 200 pieces of bones in the human body can be the object of the present invention, including, but not limited to, long bones (e.g., limb bones), short bones, flat bones (e.g., sternum, rib, scapula, or ilium), sesamoid bones (e.g., patella), and irregular bones (e.g., facial skeleton or vertebra). However, the long bones (e.g., limb bones) are appropriate for correction by the method according to the present invention. The present invention is typically applicable to malunited bones.

The bone treatment assistance device manufacturing program may be provided to the user in a desired format. For example, the program may be distributed to the users in a form of a recording medium having the program recorded thereon, or by allowing the users to download the program to the user's terminal device through a network. The bone treatment assistance device manufacturing program may be provided either for a fee or free of charge. Examples of the recording medium on which the program may be recorded include a flexible disk, an MO disk, a DVD, or any other desired recording medium. In addition, any desired network, including the internet, may be employed.

In the present description, the term "bone" refers to the support organ of a spinal animal including the individual elements of the endoskeleton. The bones of the spinal animal are primarily constituted of bone tissue, except for cyclostomes and cartilaginous fishes. The present description is also applicable to a cartilage. In the present description, when a hard connective tissue constituting the majority of the skeleton of the spinal animal is specifically referred to, the term "hard bone" is employed. It may also be understood that, although the bone is taken up as object of the present description, the method and the device of the present invention are equally applicable to other parts of the body than the bones.

In the present description, the "treatment" of the bone refers to applying a physical effect to the bone, including, but not limited to, rotation, excision, cutting, graft insertion, extension, and fixing.

In the present description, the term "patient" refers to a subject, to whom/which the treatment according to the embodiments may be applied. Preferably, the patient or subject may be a human.

In the present description, the "cutting" of the bone refers to dividing a bone into two or more parts. The cutting of the bone is typically performed with a bone cutting device such as a bone saw. In the present description, a part where the bone is cut may also be referred to as "osteotomy section".

In the present description, "fixing" a bone (bone piece) refers to substantially maintaining, after a treatment is performed, the condition obtained through the treatment. Generally, the fixing of the bone is performed with the treated bone alone.

The invention claimed is:

1. An osteotomy assistance kit comprising:
an attaching position confirmation device; and
a bone treatment assistance device,
wherein the attaching position confirmation device is attached to the bone treatment assistance device, and is configured to be employed in assisting with a cutting or perforating operation of a bone, to confirm the attaching position of the bone treatment assistance device on the bone, the attaching position confirmation device comprising:
a feature point indication rod configured to be applied via a tip portion to a predetermined specific feature point of the bone;
a rod support unit including a rod support member that supports the feature point indication rod in a posture that allows the tip portion to indicate the feature point of the bone, and an elongate member extending in an elongate shape from the rod support member, and the elongate member including a plurality of scales provided at different positions along an extending direction of the elongate member; and
a second support member that supports, when attached to the bone treatment assistance device attached to the bone, the rod support unit so as to be configured to move in the extending direction, and the second support member indicates one of the plurality of scales, wherein the bone treatment assistance device includes:
a cutting slit formed at a position corresponding to a cutting cross-section, where a bone is cut and divided when the bone treatment assistance device is attached to a surface of the bone, to guide a saw to the cutting cross-section;
guide holes, each configured to guide a first rod to be inserted in the bone when the bone treatment assistance device is attached to the surface of the bone, in a posture that the first rod inserted in a bone piece assumes a predetermined positional relation with respect to another first rod inserted in the bone piece, after bone pieces cut and divided along the cutting cross-section are corrected to a target correction position representing a normal condition; and
a fitting surface that is formed in a portion to be opposed to the bone and is configured to fit to a surface of the bone,
wherein when the rod support unit supporting the feature point indication rod being applied via the tip portion to the feature point on the bone is attached to the second support member that is attached to the bone treatment assistance device attached to the bone, the one of the plurality of scales indicated by the second support member indicates a distance from a position indicating a feature point on the bone to the bone treatment assistance device whose portion indicating the fitting surface is attached to a position that fits to a surface shape of the uncorrected bone.

2. An osteotomy assistance kit comprising:
an attaching position confirmation device; and
a bone treatment assistance device,
wherein the attaching position confirmation device is attached to the bone treatment assistance device, and is configured to be employed in assisting with a cutting or perforating operation of a bone, to confirm the attaching position of the bone treatment assistance device on the bone, the attaching position confirmation device comprising:
a feature point indication rod configured to be applied via a tip portion to a predetermined specific feature point of the bone;
a rod support unit including a rod support member that supports the feature point indication rod in a posture that allows the tip portion to indicate the feature point of the bone, and an elongate member extending in an elongate shape from the rod support member, and the elongate member including a plurality of scales provided at different positions along an extending direction of the elongate member; and
a second support member that supports, when attached to the bone treatment assistance device attached to the bone, the rod support unit so as to be configured to move in the extending direction, and the second support member indicates one of the plurality of scales,
wherein the bone treatment assistance device includes:
a cutting slit formed at a position corresponding to a cutting cross-section, where a bone is cut and divided when the bone treatment assistance device is attached to a surface of the bone, to guide a saw to the cutting cross-section; and
guide holes, each configured to guide a first rod to be inserted in the bone when the bone treatment assistance device is attached to the surface of the bone, in a posture that the first rod inserted in a bone piece assumes a predetermined positional relation with respect to another first rod inserted in the bone piece, after bone pieces cut and divided along the cutting cross-section are corrected to a target correction position representing a normal condition,
wherein the guide holes of the bone treatment assistance device each includes a protrusion protruding from a surface of the bone treatment assistance device in a direction that allows the first rod to be guided in the posture,
the second support member of the attaching position confirmation device includes a recess in which the protrusion of each of the guide holes is to be fitted, and
by fitting any one of the protrusions of the guide holes in the recess formed in the second support member, the attaching position confirmation device is attached to the bone treatment assistance device.

\* \* \* \* \*